United States Patent [19]

Jones et al.

[11] Patent Number: 4,666,909
[45] Date of Patent: May 19, 1987

[54] BISBENZOTHIAZINE, BISBENZODIAZINE AND BISQUINOLINE PHARMACEUTICAL COMPOSITIONS AND USE

[75] Inventors: Howard Jones, Ossining; Ernest Magnien, Flushing, both of N.Y.; John H. Musser, Malvern, Pa.; Mujahid L. Shaikh, White Plains, N.Y.

[73] Assignee: USV Pharmaceutical Corp., Fort Washington, Pa.

[21] Appl. No.: 762,461

[22] Filed: Sep. 16, 1985

Related U.S. Application Data

[62] Division of Ser. No. 629,285, Jul. 9, 1984, Pat. No. 4,552,876.

[51] Int. Cl.$^4$ .................. A61K 31/47; A61K 31/535; A61K 31/54
[52] U.S. Cl. .................. 514/225; 514/249; 514/312; 514/314; 544/51; 544/52; 544/353; 544/354; 546/152; 546/155; 546/158; 546/166
[58] Field of Search ............. 544/51, 52, 353, 354; 546/152, 155, 158, 166; 514/225, 249, 312, 314

[56] References Cited

U.S. PATENT DOCUMENTS 4,420,613 12/1983 Uhrhan et al. ................. 544/51

FOREIGN PATENT DOCUMENTS 127762 12/1984 European Pat. Off. .

OTHER PUBLICATIONS

Stewart, Journal of Organic Chemistry, vol. 26, (1961), pp. 3604-3605.
Barker et al, J. Chem. Soc. (B), 1969, pp. 1068-1071.
Castelin et al, J. Chem. Soc. (B), 1971, pp. 1468-1471.
Ishidate et al, Chemical Abstracts, vol. 69, (1968) 35674z.
Uhrhan et al, Chemical Abstracts, vol. 98 (1983) 73380g.

*Primary Examiner*—Richard L. Raymond

[57] ABSTRACT

Compounds of the formula:

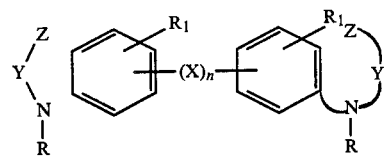

wherein,
R is H, alkyl, cycloalkyl, aryl or heteroaryl;
$R_1$ is H, alkyl, cycloalkyl, aryl, heteroaryl, substituted heteroaryl, aralkyl, substituted aryl, halo, $OR^2$, $SR^2$, $NR_2$, $CF_3$, $NO_2$, $CN$, $COOR^2$, $CHO$, $SO_3H$ or $SO_2NH_2$, wherein
$R^2$ is H, methyl, ethyl or propyl;
Y is

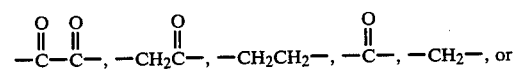

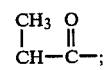

Z is O, S, NH or $CH_2$;
X is

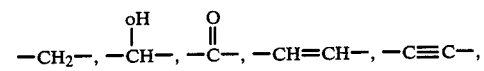

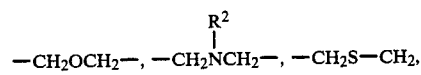

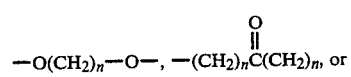

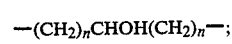

wherein
$R^2$ is H, methyl, ethyl or propyl;
n is 1–10, and pharmaceutically acceptable salts thereof have antiallergy and antiinflammatory activity.

8 Claims, No Drawings

BISBENZOTHIAZINE, BISBENZODIAZINE AND BISQUINOLINE PHARMACEUTICAL COMPOSITIONS AND USE

This application is a division of copending application Ser. No. 629,285, filed July 9, 1984, now U.S. Pat. No. 4,552,876.

This invention relates to new pharmaceutically-active compounds and more particularly to certain new bisbenzoxazoles and bisbenzoxazines possessing useful pharmaceutical activities, especially anti-allergy and anti-inflammatory activity.

The new compounds of the present invention have the formula:

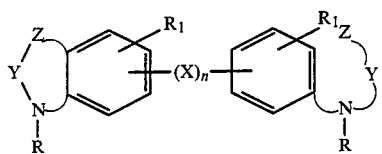

and pharmaceutically acceptable salts thereof, wherein,
R is H, alkyl, cycloalkyl, aryl, or heteroaryl;
$R_1$ is H, alkyl, cycloalkyl, aryl, heteroaryl, substituted heteroaryl, aralkyl, substituted aryl, halo, $OR^2$, $SR^2$, $NR_2$, $CF_3$, $NO_2$, CN, $COOR^2$, CHO, $SO_3H$ or $SO_2NH_2$,
wherein
$R^2$ is H, methyl, ethyl or propyl;
Y is

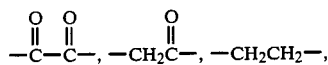

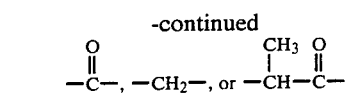

X is

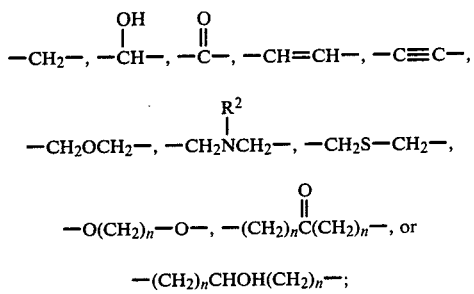

wherein
$R^2$ is H, methyl, ethyl or propyl; and
n is 1–10, and pharmaceutically acceptable salts thereof.

The alkyl group in alkyl contains from 1 to 10 carbon atoms, preferably 1 to 5 carbon atoms and may be straight or branched.

The cycloalkyl groups contain from 3 to 7 carbon atoms.

The aryl group in aryl and substituted aryl is preferably phenyl or naphthyl.

The heteroaryl group in heteroaryl and substituted heteroaryl is preferably thiophenyl, pyridyl or quinolyl.

The substituents in substituted aryl and substituted heteroaryl are H, methyl, ethyl or propyl.

The present new compounds are readily preparable by art-recognized procedures. A particularly effective procedure, using the starting material anisole, obtained from Aldrich Chem. Co., is illustrative of procedures leading to the synthesis of compounds of the present invention.

SYNTHESIS OF COMPOUNDS

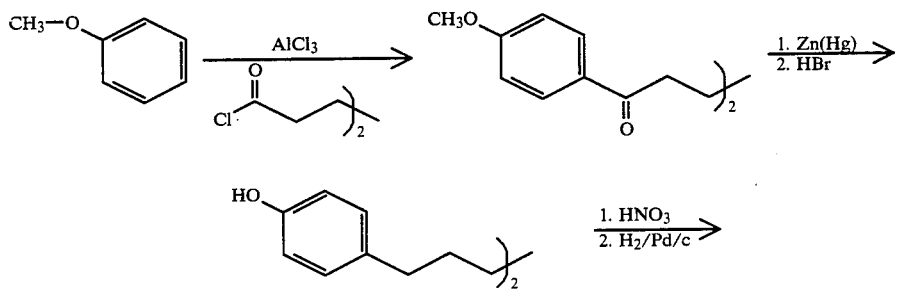

-continued
SYNTHESIS OF COMPOUNDS

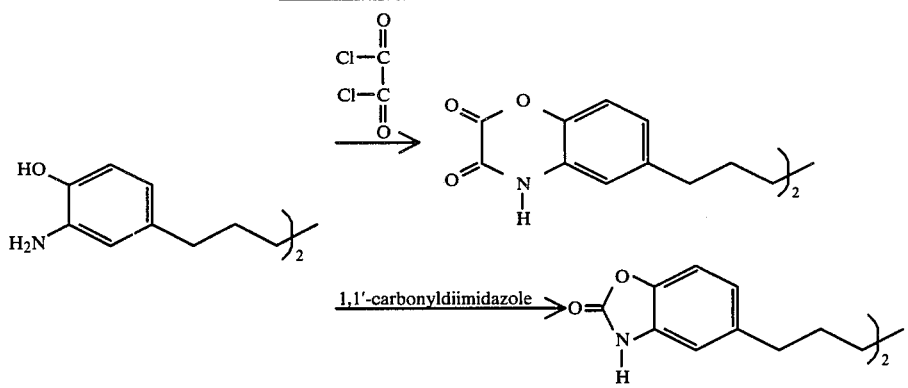

Examples of other starting materials, which are also available from chemical supply companies, such as Aldrich Chem. Co., include: methoxynaphthalene, methoxypyridine and methoxyquinoline.

Compounds of the present invention were found to be effective anti-allergic and anti-inflammatory agents.

In general, the substance of this invention is administered in analogy to known, commercially available formulations with a similar indication in dosages of approximately 1 to 200 mg per dosage unit or higher. The daily dosage is approximately 0.02–5 mg/kg of body weight. It is to be understood, however, that the particular dose for each patient as usual depends on very diverse factors, such as the age, body weight, general condition of health, sex, diet, and the like of the patient, on the time and route of administration, or the rate of excretion, on the combination of medicaments and on the severity of the particular disease to which therapy relates.

The compounds of the present invention may be administered enterally, parenterally or topically. The compound may be incorporated into pharmaceutical formulations having excipients suitable for these administrations and which do not adversely react with the compounds, for example, water, vegetable oils, certain alcohols and carbohydrates, gelatin, magnesium stearate, talc, cornstarch or petroleum jelly. The pharmaceutical formulations containing an active compound of the present invention may be made into: tablets, capsules, elixirs, drops or suppositories for enteral administration; solutions, suspensions or emulsions for parenteral administration; ointments, creams or powders for topical application, and inhalation capsules, sprays, nasal and eye drops.

The following examples will further illustrate the invention. Examples 1–20 show the synthesis of intermediates used for preparing the compounds of the present invention. Examples 21–34 present the preparation of the novel compounds of the present invention.

EXAMPLE 1

1,6-Bis(4-methoxyphenyl)hexa-1,6-dione

A mixture of anisole (81.0 g, 0.75 mole), anhydrous aluminum chloride and chloroform (150 ml) was treated with adipoyl chloride (67.5 g, 0.37 mole) over a period of 30 minutes. The reaction mixture was heated to reflux for 1.5 hours. Then the reaction mixture was poured into crushed ice. Excess ether was added to give a white precipitate which was filtered and washed with water and ether and dried in vacuo to give 110 g of white solid, mp. 136° C.

EXAMPLE 2

1,6-Bis(4-methoxyphenyl)hexane

A mixture of 60 g of 1,6-bis(4-methoxyphenyl)hexa-1,6-dione of Example 1, 240 g of amalgamated zinc, 300 ml of concentrated hydrochloric acid, 100 ml of water and 125 ml of toluene was heated under reflux for 30 hours and a further 100 ml of concentrated hydrochloric acid was added after the first 8 hours. After cooling to room temperature, ethyl acetate (300 ml) was added. The organic phase was separated and washed with water, saturated sodium chloride, dried over anhydrous magnesium sulfate and concentrated to give 53.5 g of semi-solid material.

EXAMPLE 3

1,6-Bis(4-hydroxyphenyl)hexane

A mixture 40.0 g of 1,6-bis(4-methoxyphenyl)hexane of Example 2, 150 ml of HBr (48%) and 150 ml of glacial acetic acid was refluxed for 5 hours. It was concentrated by evaporation to give a dark brown semi-solid. This was dissolved in ether, washed with water, dried over anhydrous magnesium sulfate and concentrated to give 28.0 g of dark brown semi-solid.

EXAMPLE 4

1,6-Bis(4-hydroxy-3-nitrophenyl)hexane

To a solution of 17 g of 1,6-bis(4-hydroxyphenyl)hexane of Example 3 in 150 ml of ether was added 7.6 ml of concentrated nitric acid all at once. After refluxing for 10 minutes, 100 ml of ethyl acetate was added. The organic layer was washed with water and dried over magnesium sulfate. The residue after removal of solvent was chromatographed on a silica gel column using hexane:ethyl acetate (88:12) as eluent to give 14.0 g of yellow solid.

EXAMPLE 5

1,6-Bis(3-amino-4-hydroxyphenyl)hexane

A solution of 7.0 g of 1,6-bis(4-hydroxy-3-nitrophenyl)hexane of Example 4 in ethyl acetate:methanol (3:1) and 400 mg of 5% palladium on carbon was hydrogenated on a Parr hydrogenation apparatus for 3 hours. After filtration and removal of solvent, 5.6 g of off-white solid was obtained.

EXAMPLE 6

1,5-Bis(4-methoxyphenyl)penta-1,4-diene-3-one

A mixture of p-anisaldehyde (136 g, 1 mole) and acetone (29 g, 0.5 mole) was added slowly to a solution of sodium hydroxide (100 g, 2.5 mole) in 700 ml of water containing 600 ml of ethanol. The reaction mixture was stirred mechanically for two hours. A yellow solid separated which was filtered, washed with excess water and dried in vacuo to give 70 g of yellow crystalline solid.

EXAMPLE 7

1,5-Bis(4-methoxyphenyl)pentan-3-one

A mixture of 1,5-bis(4-methoxyphenyl)penta-1,4-diene-3-one of Example 6 (20 g, 0.068 mole), glacial acetic acid (200 ml) and 3.0 g of palladium/carbon (5%) was hydrogenated on a Parr hydrogenator for 4 hours. The solution was filtered and concentrated to give 18.5 g of colorless liquid.

EXAMPLE 8

1,5-Bis(4-methoxyphenyl)pentane

A mixture of 1,5-bis(4-methoxyphenyl)pentan-3-one of Example 7 (57 g, 0.19 mole), amalgamated zinc (200 g), dioxane (250 ml), concentrated hydrochloric acid (250 ml) and 150 ml of water was refluxed overnight. A further 50 ml of concentrated hydrochloric acid was added after the first 6 hours. The organic layer was separated, diluted with ether, washed with water, dried over anhydrous magnesium sulfate and concentrated to give 60 g of a thick oil. NMR and mass spectra confirmed the structure.

EXAMPLE 9

1,5-Bis(4-hydroxyphenyl)pentane

A mixture of 1,5-bis(4-methoxyphenyl)pentane of Example 8 (60 g, 0.21 mole), 150 ml of hydrobromic acid (47%) and 200 ml of glacial acetic acid was refluxed for 4.5 hours. It was concentrated to a thick liquid, dissolved in ethyl acetate, washed with water, dried over anhydrous magnesium sulfate and concentrated to give 53.0 g of a thick oil. NMR and TLC confirmed the structure.

EXAMPLE 10

1,5-Bis(4-hydroxy-3-nitrophenyl)pentane

To a solution of 1,5-bis(4-hydroxyphenyl)pentane of Example 9 (18.0 g, 0.07 mole) in 150 ml of ether was added concentrated nitric acid (8.4 ml, 0.14 mole) all at once and refluxed for twenty minutes. It was diluted with 100 ml of ethyl acetate, washed with water, dried over anhydrous magnesium sulfate and concentrated to give a yellow solid. This was column chromatographed using silica gel as a support and hexane:ethyl acetate (88:12) as a solvent system. 6.6 g of yellow solid was recovered. NMR, TLC and mass spectra confirmed the structure.

EXAMPLE 11

1,5-Bis(3-Amino-4-hydroxylphenyl)pentane

A mixture of 1,5-bis(4-hydroxy-3-nitrophenyl)pentane of Example 10 (6.6 g), ethyl acetate (150 ml), methanol (50 ml) and 300 mg of palladium/carbon (5%) was hydrogenated on a Parr hydrogenator for 4 hours. Then it was diluted with 100 ml of ethyl acetate, filtered and concentrated to give 5.1 g of an off-white solid. NMR and TLC confirmed the structure.

EXAMPLE 12

1,2-Bis(4-methoxyphenyl)ethane

A mixture of 60 g of desoxyanisoin, 120 g of amalgamated zinc, 200 ml of dioxane, 100 ml of toluene and 200 ml of concentrated hydrochloric acid was refluxed for 24 hours. Another 50 ml of concentrated hydrochloric acid was added after the first 6 hours. The reaction mixture was cooled to room temperature and the organic layer was separated and mixed with 300 ml of ethyl acetate. It was washed with water, dried over anhydrous magnesium sulfate and concentrated to give 26 g of white waxy solid.

EXAMPLE 13

1,2-Bis(4-hydroxyphenyl)-ethane

A mixture of 25 g of 1,2-bis(4-methoxyphenyl)methane, 100 ml of hydrobromic acid (48%) and 100 ml of glacial acetic acid was refluxed for two hours. The solution was concentrated to a pinkish solid which on crystallization from acetonitrile gave 10 g of pinkish solid.

EXAMPLE 14

1,2-Bis(4-hydroxyl-3-nitrophenyl)ethane

To a suspension of 10 g of 1,2-bis(4-hydroxyphenyl)methane in 90% acetic acid (300 ml) at 5° C. was added 6.7 ml of concentrated nitric acid. The reaction mixture was stirred for two hours at room temperature. A yellow precipitate formed which was filtered, washed with the water and dried in vacuo to give 10 g of yellow solid.

EXAMPLE 15

1,2-Bis(3-amino-4-hydroxyphenyl)ethane

A mixture of 10 g of 1,2-bis(4-hydroxy-3-nitrophenyl)methane, 250 ml of methanol and 0.5 g of palladium on carbon (5%) was hydrogenated on a Parr hydrogenator for 4 hours. There was added 250 ml of dimethylformamide. The mixture was warmed, filtered through Celite and concentrated to give a liquid which when mixed with ether caused a solid to separate which was filtered, dried in vacuo to give 7.0 g of light brown solid.

EXAMPLE 16

1,5-Bis(4-hydroxyphenyl)penta 1,4-diene-3-one

A solution of 150 g (1.23 mole) of 4-hydroxybenzaldehyde and 30 g (0.52 mole) of acetone in 600 ml of absolute ethanol was cooled while passing in hydrogen chloride for 45 minutes. After two hours of stirring, ice water was added and the resulting dark solid was filtered off. It was crystallized from absolute ethanol to give 90 g of brown, crystalline product.

EXAMPLE 17

(a)

1,5-Bis(4-hydroxyphenyl)pentan-3-one

A mixture of 20 g (0.075 mol) of 1,5-bis(4-hydroxyphenyl)penta 1,4-diene-3-one of Example 16 in 200 ml of glacial acetic acid and 1.5 g of 5% Pd/C was placed on a Parr hydrogenator for 2 hours under hydrogen.

This reaction was repeated and the two solutions were filtered and evaporated to give a viscous oil (18 g). This was chromotographed on a silica gel column (Woelm) and eluted with CHCl₃:MeOH (95:5). The product (7.0 g) was recovered first and then 9.0 g of the corresponding alcohol.

(b)

1,5-Bis(4-hydroxy-3-nitro)pentan-3-one

A solution of 3.3 g (0.012 mol) of 1,5-bis(4-hydroxyphenyl)penta-3-one of Example 17a in 30 ml of ether was treated with 1.53 g (0.024 mol) of concentrated nitric acid all at once. After refluxing for 10 minutes and stirring at room temperature, the product was filtered and washed with ether to give 4.8 g of the title product.

EXAMPLE 18

1,5-Bis(3-amino-4-hydroxyphenyl)pentan-3-one

A solution of 8.2 g of 1,5-bis(4-hydroxy-3-nitrophenyl)pentan-3-one in 50 ml of methanol and 150 ml of ethyl acetate was placed in a Parr hydrogenator with 300 mg of 10% Pd/C. After 3 hours the solution was filtered and evaporated to dryness to give 6.7 g of product of m.p. 131°–133° C.

Anal. calcd. for $C_{17}H_{20}N_2O$: calcd C, 67.98; H, 6.71; N, 9.32. Found C, 66.91; H, 6.62; N, 8.64.

EXAMPLE 19

1,1-Bis(5-chloro-2-hydroxy-3-nitrophenyl)methane

To a solution of 54 g (0.2 mole) of 2,2-methylenebis(4-chlorophenol) in 100 ml of acetic acid and 50 ml of water was added slowly at 0° C. 27.7 g (0.44 mole) of nitric acid. The reaction mixture was allowed to come to room temperature. The precipitate which formed was filtered off and washed with water to give 71.3 g of yellow solid of m.p. 163°–170° C.

EXAMPLE 20

1,1-Bis(3-amino-5-chloro-2-hydroxyphenyl)methane

To a suspension of 36.3 g (0.1 mole) of 1,1-bis(5-chloro-2-hydroxy-3-nitrophenyl)methane of Example 19 in 300 ml of methanol-water (1:1) was added 145 g (0.4 mole) of sodium dithionate. The mixture was stirred for 4 hours and then filtered. The solid was dissolved in 22 g of ethyl acetate and washed with water, dried over magnesium sulfate and concentrated to yield 16.9 g of product of m.p. 212°–215° C.

EXAMPLE 21

1,5-Bis(benzoxazin-2,3-dione-6yl)pentane

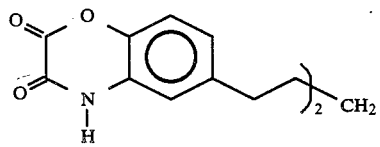

To a solution of 7.3 g (0.0576 mole) of oxalyl chloride in 50 ml of o-dichlorobenzene was added a hot solution of 7.5 g (0.026 mole) of 1,5-bis(3-amino-4-hydroxyphenyl)pentane in 150 ml of o-dichlorobenzene. After stirring for 1 hour at reflux the reaction mixture was filtered and allowed to stand overnight in the refrigerator. The precipitate was filtered and washed with ether. This material was suspended and refluxed in ether for 3 hours. On filtration, there was obtained 5.7 g of product.

Anal. calcd. for $C_{21}H_{12}N_2O_6$: Calcd. C, 63.96; H, 4.60; N, 7.10. Found C, 63.91; H, 4,82; N, 6.86.

EXAMPLE 22

1,6-Bis(benzoxazine-2,3-dione-6yl)hexane

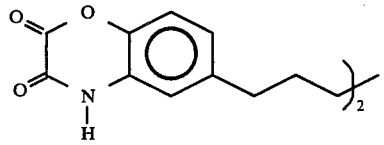

To a solution of 4.1 g (0.032 mole) of oxalyl chloride in 60 ml of o-dichlorobenzene at 65° C. was added 4.4 g (0.0147 mole) of 1,6-bis(3-amino-4-hydroxyphenyl)hexane portionwise over 15 minutes. The mixture was refluxed for 15 minutes, filtered hot. The brown crystalline solid was dissolved in acetone, concentrated and treated with ether. The product was filtered off and washed with ether to yield 1.8 g of product.

Anal. Calcd. for $C_{22}H_{20}N_2O_6 \cdot \frac{1}{2}H_2O$: Calcd. C, 63.30; H, 5.07; N, 6.71. Found C, 63.00; H, 5.09; N, 5.91.

EXAMPLE 23

1,5-Bis[2H-1,4-benzoxazine-3(4H)-one-6yl]pentane

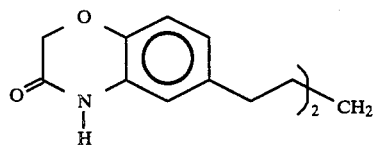

To a suspension of 1.5 g of 1,5-bis(3-amino-4-hydroxyphenyl)pentane (0.0052 mol) in 7 ml of isobutyl methyl ketone was added 1.05 g (0.0125 mole) of sodium bicarbonate and 5 ml of water. The suspension was stirred in an ice bath and 1.4 g (0.0124 mole) of chloroacetyl chloride was added dropwise. After addition, the mixture was allowed to come to room temperature and then was refluxed for 4 hours. After cooling, the resulting crystalline solid was filtered and washed with acetone to yield 0.4 g of off-white product of m.p. 189°–190° C.

Anal. Calcd. for $C_{21}H_{22}N_2O_4 \cdot \frac{1}{2}H_2O$: Calcd. C, 67.19; H, 6.17; N, 7.45. Found C, 67.10; H, 5.98; N, 6.84.

EXAMPLE 24

1,6-Bis[2H-1,4-benzoxazine-3(4H)-one-6yl]hexane

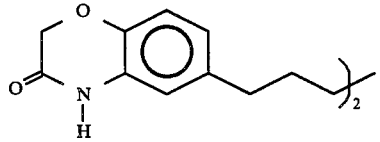

To a suspension of 2.1 g (0.007 mol) of 1,6-bis(3-amino-4-hydroxyphenyl)hexane in 10 ml of isobutyl methyl ketone was added 3.0 g (0.0357 mole) of sodium bicarbonate and 10 ml of water. The suspension was stirred in an ice bath and 1.9 g (0.016 mole) of chloroacetyl chloride was added dropwise. The reaction was carried out in a manner similar to that in Example 23 to yield 1.0 g of product of m.p. 219°–225° C.

EXAMPLE 25

1,2-Bis[2H-1,4-benzoxazin-3(4H)-one-6yl]ethane

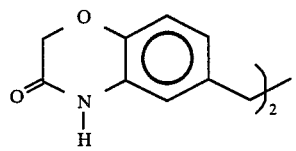

To 3.0 g (0.0123 mole) of 1,2 bis(3-amino-4-hydroxyphenyl)ethane in 25 ml of isobutyl methyl ketone was added 5.0 g (0.06 mole) sodium bicarbonate and 25 ml of water. The mixture was cooled in an ice-bath and 1.4 g (0.012 mole) of chloroacetyl chloride was added dropwise over 15 minutes. After coming to room temperature, the mixture was refluxed for 4 hours. On cooling, the solid was filtered off and washed with acetone. The precipitate was suspended in acetone, refluxed for 15 minutes and cooled. On filtration, there was obtained 2.3 g of a beige solid.

Anal. Calcd. for $C_{18}H_{16}N_2O_4 \cdot \tfrac{1}{2}H_2O$: Calcd. C, 64.85; H, 5.14; N, 8.40. Found C, 65.19; H, 5.05; N, 8.06.

EXAMPLE 26

1,6-Bis[2H-1,4-benzoxazine-2-methyl-3(4H)-one-6yl]hexane

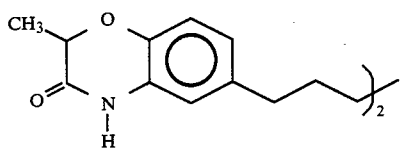

A mixture of 3.0 g (0.01 mole) of 1,6-bis(3-amino-4-hydroxyphenyl)hexane, 2.54 g (0.02 mol) of 2-chloropropionyl chloride and 3.0 g (0.022 mole) of potassium carbonate in 20 ml of dimethylformamide was stirred at 115° C. for two hours. Addition of water to the cooled reaction mixture gave a brown solid which was washed with water and then crystallized from ethanol to give 1.2 g of a solid which was crystallized from acetonitrile to give 0.8 g of an intermediate. This was heated with 0.5 g of potassium carbonate, 0.1 g of potassium iodide and 10 ml of dimethylformamide to 160° C. for 4 hours. Water was added to the cooled reaction mixture. The product precipitated and was filtered and washed with water until free of ionic halogen to yield 0.4 g of tan product of m.p. 215°–217° C.

Anal. calcd. for $C_{24}H_{28}N_2O_4 \cdot \tfrac{1}{2}H_2O$: Calcd. C, 69.04; H, 7.00; N, 6.71. Found C, 69.40; H, 6.73; N, 6.49.

EXAMPLE 27

1,5 Bis[2H-1,4-benzoxazin-3(4H)-one-5yl]-pentane-3-one

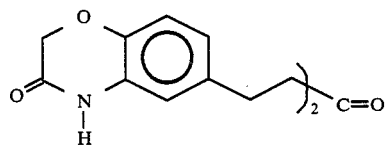

To a suspension of 1,5-bis[3-amino-4-hydroxyphenyl]pentan-3-one (3.0 g, 10.0 mmole), sodium bicarbonate (4.2 g, 50 mmole) and 4-methyl-2-pentanone (20 ml) chloroacetyl chloride (2.8 g, 0.025 mole) was added dropwise. It was refluxed for 4 hours, cooled to room temperature, filtered, washed with water and acetone. The solid was dried in vacuo to give 3.1 g of beige product of m.p. 183°–185° C.

Anal. calcd. for $C_{21}H_{20}N_2O_5 \cdot \tfrac{1}{4}H_2O$: Calcd. C, 65.53; H, 5.37; N, 7.28. Found C, 65.40; H, 5.4; N, 7.11.

EXAMPLE 28

1,5-Bis[benzoxazolino-2-one-5yl]pentan-3-ol

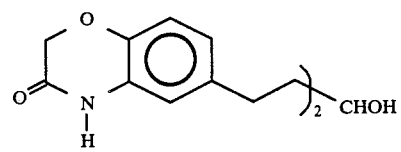

To a solution of 1,5-bis[2H-1,4-benzoxazin-3(4H)-one-5yl]pentan-3-one (1.3 g, 3.42 mmole) in dimethyl sulfoxide (25 ml), sodium borohydride (0.65 g, 17.1 mmole) was added portionwise over a period of 15 minutes at 0°–5° C. The mixture was stirred for 4 hours at 5°–10° C. After the reaction was over, it was mixed with excess of ether and decanted. The solid left behind was mixed with water, filtered, washed with water and ether, then dried in vacuo to give 0.8 g of beige solid m.p. 185°–187° C.

Anal. calcd. for $C_{21}H_{22}N_2O_5 \cdot \tfrac{1}{2}H_2O$: Calcd. C, 62.99; H, 6.04; N, 6.99. Found C, 63.12; H, 5.86; N, 6.92.

EXAMPLE 29

1,5-Bis[benzoxazolino-2-one-5yl]pentane

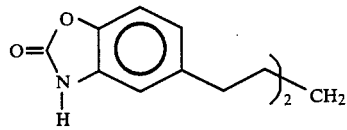

To 2.5 g (0.0087 mole) of 1,5-bis(3-amino-4-hydroxyphenyl)pentane in 50 ml of tetrahydrofuran was added 4.2 g (0.026 mole) of 1,1-carbonyldiimidazole. The mixture was stirred and refluxed for 4 hours. The residue after removal of the solvent, was partitioned between 5% hydrochloric acid and ethyl acetate. The organic layer was dried and concentrated to give 0.6 g of an off-white product of m.p. 158°–161° C.

Anal. calcd. for $C_{19}H_{18}N_2O_4 \cdot \tfrac{1}{2}H_2O$: Calcd. C, 65.70; H, 5.51; N, 8.06. Found C, 65.35; H, 5.40; N, 7.73.

EXAMPLE 30

1,6-Bis(benzoxazolino-2-one-5yl)hexane

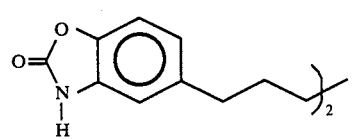

A mixture of 1.0 g (0.003 mole) of 1,6-bis(3-amino-4-hydroxyphenyl)hexane and 1.6 g (0.01 mole) of 1,1′-carbonyldiimidazole in 25 ml of dry tetrahydrofuran was refluxed and stirred for 5 hours. The solvent was evaporated and the residue was partitioned between ethyl acetate and 1N hydrochloric acid. The organic layer was dried and evaporated to yield 0.8 g of product of m.p. 205°–210° C.

Anal. calcd. for $C_{20}H_{20}N_2O_4$: Calcd. C, 68.17; H, 5.72; N, 7.95. Found C, 67.63; H, 5.72; N, 7.33.

EXAMPLE 31

1,2-Bis[benzoxazolino-2-one-5yl]ethane

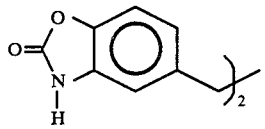

A mixture of 2.0 g (0.0082 mole) of 1,2-bis(3-amino-4-hydroxyphenyl)ethane, 2.0 g (0.0125 mole) of 1,1′-carbonyldiimidazole and 40 ml of tetrahydrofuran was refluxed for 4 hours. The solvent was removed and the residue was partitioned between 1N hydrochloric acid and ethyl acetate. The organic layer was dried and concentrated. On cooling and filtering, 1.1 g of product was obtained as a light brown solid of m.p. 235°–240° C.

Anal. calcd. for $C_{16}H_{12}N_2O_4.\frac{1}{2}H_2O$: Calcd. C, 63.00; H, 4.30; N, 9.18. Found C, 63.01; H, 4.66; N, 8.39.

EXAMPLE 32

1,5-Bis(benzoxazolino-2-one-5yl)pentan-3-one

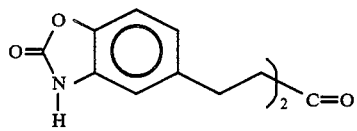

A mixture of 2.5 g (0.0083 mole) of 1,5-bis(3-amino-4-hydroxyphenyl)pentan-3-one and 4.0 g (0.0248 mole) of 1,1′-carbonyldiimidazole in 50 ml of tetrahydrofuran was refluxed for 3.5 hours. The residue after concentration was partitioned between ethyl acetate and 1N hydrochloric acid. The organic layer was dried and concentrated to give 2.5 g of a light tan solid of m.p. 180°–182° C.

Anal. calcd. for $C_{19}H_{16}N_2O_5$: Calc. C, 64.77; H, 4.58, N, 7.95. Found C, 64.37; H, 4.83; N, 7.55.

EXAMPLE 33

1,5-Bis(benzoxazolino-2-one-5yl)pentan-3-ol

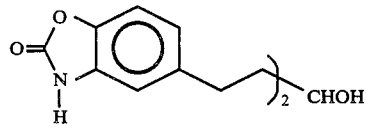

To a solution of 1,5-bis(benzoxazolino-2-one-5yl)-pentane-3-one (1.0 g, 2.8 mmole) in dimethyl sulfoxide (25 ml), sodium borohydride (0.5 g, 14.0 mmole) was added portionwise over a period of 15 minutes at 5° C. The mixture was stirred for additional 3.5 hours at 5°–10° C. Excess ether was added and then decanted from a thick gum which was formed. This was dissolved in ethyl acetate. The solution was dried over magnesium sulfate and concentrated to give 0.5 g of a yellow solid of m.p. 185°–188° C.

Anal. calcd. for $C_{19}H_{18}N_2O_5.\frac{1}{2}H_2O$: Calcd. C, 62.80; H, 5.27; N, 7.70. Found C, 62.60; H, 5.24; N, 7.28.

EXAMPLE 34

1,1-Bis[2H-1,4-benzoxazin-3-(4H)-one-6-chloro-8yl]methane

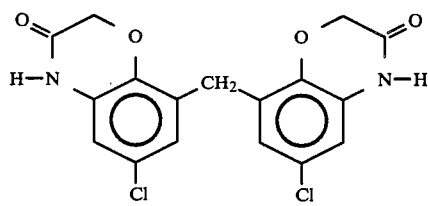

To a suspension of 1.5 g (0.005 mole) of 1,1-bis(3-amino-5-chloro-2-hydroxyphenyl)methane in 10 ml of isobutyl methyl ketone was added 2.1 g (0.025 mole) of sodium bicarbonate and 10 ml of water. The mixture was cooled in an ice bath and 1.4 g (0.0124 mole) of chloroacetyl chloride was added dropwise over 10 minutes. The mixture was refluxed for 4 hours. On cooling, the product crystallized and was filtered off and washed with acetone. This was crystallized from acetone-hexane to yield 0.5 g of product of m.p. 295° C.

Anal. Calcd. for $C_{17}H_{12}Cl_2N_2O_4$: Calcd. C, 53.85; H, 3.19; N, 7.38. Found C, 53.45; H, 3.59; N, 7.06.

Compounds of the present invention identified in Examples 21–34 were tested in the assay described below.

RAT AND DOG PHOSPHOLIPASE INHIBITION

The protocol is based on the article, "Relative Activities of Rat and Dog Platelet Phospholipase $A_2$ and Diglyceride Lipase", C. A. Sutherland and D. Amin, *J. Biol. Chem.* 257 14006–14010 (1982).

Platelets were obtained from rat and dog blood. The platelet pellets obtained by centrifugation of the citrated blood were dispersed in three volumes of TAPS-NC ($16 \times 10^6$ cells/ml). Soluble enzymes were separated from platelet membranes, after cell lysis, by centrifugation. The enzyme standard for the phospholipase $A_2$ determination was Naja naja venom, Sigma P-6139.

Substrates were dissolved or suspended in dimethyl sulfoxide and incubated at 37° C. for 30 minutes with the platelets at pH7 and pH9. The reaction was terminated by additions of 1N HCl. Diglycerol lipase activity was monitored by recovery of $^{14}C$-free fatty acid released by the enzyme from [1,2-dipalmitoyl-1-$^{14}C$]glycerol. Results obtained are shown in Table I.

TABLE I

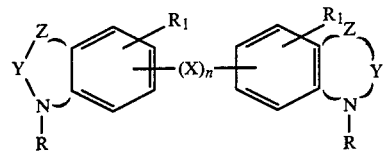

| Example | Y | X | PHOSPHOLIPASE A2 INHIBITION (I50 μM) pH7 | pH9 |
|---|---|---|---|---|
| 21 | ⟩=O, ⟩=O | —(CH2)5— | 8.6 | 49 |
| 22 | ⟩=O, ⟩=O | —(CH2)6— | 6.1 | 30 |
| 23 | ⟩, ⟩=O | —(CH2)5— |  | 50 |
| 24 | ⟩, ⟩=O | —(CH2)6— |  | 12 |
| 25 | ⟩, ⟩=O | —(CH2)2— |  | 40 |
| 27 | ⟩, ⟩=O | —(CH2)2—C(=O)—(CH2)2— |  | 30 |
| 28 | ⟩, ⟩=O | —(CH2)2—CHOH—(CH2)2— | 37 | 35 |
| 29 | ⟩C=O | —(CH2)5— | 64 | 84 |
| 31 | ⟩C=O | —(CH2)2— |  | 70 |
| 32 | ⟩C=O | —(CH2)2—C(=O)—(CH2)2— |  | 185 |

As can be readily ascertained from the foregoing, the compounds of the present invention are effective in inhibiting the interaction of antibodies and cells believed to participate in causing allergic reactions, as well as inhibiting the allergic secretion of histamine from histamine-containing cells. As such, the compound of the present invention may be used in preventive treatment of the human or animal body and in combating diseases, in particular several forms of allergic and asthmatic diseases, specifically asthma bronchial, allergic bronchitis, asthmatic bronchitis, food allergy, hay fever allergic rhinitis and allergic conjunctivitis.

Having described the invention, it will be apparent to one of ordinary skill in the art that changes and modifications can be made thereto without departing from the spirit and scope of the invention as set forth herein.

What is claimed is:

1. A pharmaceutical composition for the treatment of allergic or inflammatory conditions comprising as an active ingredient a member of the formula

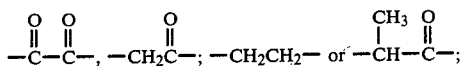

wherein,
R is H, alkyl, cycloalkyl, aryl, or heteroaryl; $R_1$ is H, alkyl, cycloalkyl, aryl, heteroaryl, aralkyl, substituted aryl, substituted heteroaryl, halo, $OR^2$, $SR^2$, $NR_2$, $CF_3$, $NO_2$, CN, $COOR^2$, CHO, $SO_3H$ or $SO_2NH_2$, wherein,
the substitutents in substituted aryl and substituted heretoaryl are H, methyl, ethyl or propyl;
$R^2$ is H, methyl, ethyl or propyl;
Y is $$-\overset{O}{\underset{\|}{C}}-\overset{O}{\underset{\|}{C}}-,\ -CH_2\overset{O}{\underset{\|}{C}}-;\ -CH_2CH_2-\ \text{or}\ -\overset{CH_3}{\underset{|}{CH}}-\overset{O}{\underset{\|}{C}}-;$$

Z is S, NH or $CH_2$;
X is $$-CH=CH-,\ -C\equiv C-,\ -CH_2OCH_2-,\ -CH_2\overset{R^2}{\underset{|}{N}}CH_2-,$$

$$-CH_2S-CH_2-,\ -O-(CH_2)_n-O-,$$

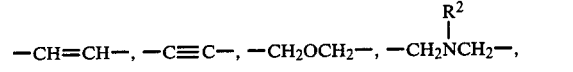

wherein,
$R^2$ is H, methyl, ethyl or propyl; and
n is 1-10, or pharmaceutically acceptable salts thereof, in a pharmaceutically acceptable carrier;
wherein said pharmaceutically acceptable carrier is in the form of tablets, capsules, elixirs, drops or suppositories for enteral administration; suspensions or emulsions for parenteral administration; ointments, creams or powders for topical administration; and inhalation capsules, sprays, nasal or eye drops.

2. The pharmaceutical composition of claim 1 wherein the alkyl group in R and $R_1$ contains from 1 to 10 carbon atoms.

3. The pharmaceutical composition of claim 2 wherein said alkyl group is a straight chain.

4. The pharmaceutical composition of claim 2 wherein said alkyl group is branched.

5. The pharmaceutical composition of claim 1 wherein said cycloalkyl contains from 3 to 7 carbon atoms.

6. The pharmaceutical composition of claim 1 wherein said aryl in aryl and substituted aryl is phenyl or naphthyl.

7. The pharmaceutical composition of claim 1 wherein said heteroaryl in heteroaryl and substituted heteroaryl is thiophene, pyridyl or quinolyl.

8. A method of treating allergic or inflammatory conditions in a mammal comprising: administering to said mammal an effective amount of a composition to relieve such allergic or inflammatory conditions, said composition comprising as an active ingredient a member of the formula

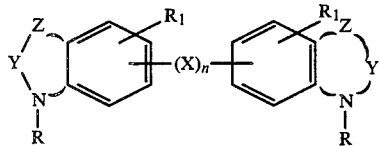

wherein,

R is H, alkyl, cycloalkyl, aryl, or heteroaryl;

$R_1$ is H, alkyl, cycloalkyl, aryl, heteroaryl, aralkyl, substituted aryl, substituted heteroaryl, halo, $OR^2$, $SR^2$, $NR_2$, $CF_3$, $NO_3$, CN, $COOR^2$, CHO, $SO_3H$ or $SO_2NH_2$, wherein, the substituents in substituted aryl and substituted heteroaryl are H, methyl, ethyl or propyl $R^2$ is H, methyl, ethyl or propyl;

Y is

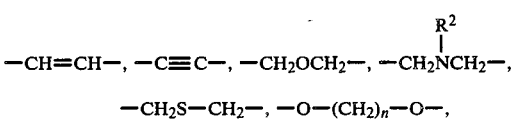

Z is S, NH or $CH_2$;

X is

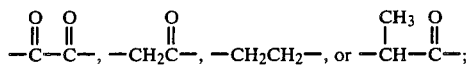

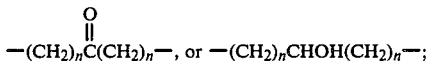

wherein, $R^2$ is H, methyl, ethyl or propyl; and n is 1–10, or pharmaceutically acceptable salts thereof, in a pharmaceutically acceptable carrier.

* * * * *